(12) United States Patent
Fleche et al.

(10) Patent No.: US 7,122,661 B2
(45) Date of Patent: Oct. 17, 2006

(54) METHOD FOR PURIFYING A COMPOSITION CONTAINING AT LEAST ONE INTERNAL DEHYDRATION PRODUCT OF A HYDROGENATED SUGAR

(75) Inventors: Guy Fleche, Hazebrouck (FR); Patrick Fuertes, Lambersart (FR); Rodolphe Tamion, Allouagne (FR); Hervé Wyart, Cuinchy (FR)

(73) Assignee: Roquette Freres, Lestrem (FR)

( * ) Notice: Subject to any disclaimer, the term of this patent is extended or adjusted under 35 U.S.C. 154(b) by 52 days.

(21) Appl. No.: 10/313,286

(22) Filed: Dec. 6, 2002

(65) Prior Publication Data

US 2004/0110969 A1    Jun. 10, 2004

Related U.S. Application Data

(63) Continuation of application No. PCT/FR01/01676, filed on May 30, 2001.

(30) Foreign Application Priority Data

Jun. 9, 2000   (FR) .................................. 00 07463

(51) Int. Cl.
C07D 307/02   (2006.01)
(52) U.S. Cl. ...................................... 536/124; 549/475
(58) Field of Classification Search ................ 536/124, 536/126, 123.1, 55.3, 18.5, 18.6, 4.1
See application file for complete search history.

(56) References Cited

U.S. PATENT DOCUMENTS

| | | |
|---|---|---|
| 3,160,641 A | 12/1964 | Hartmann et al. |
| 3,223,752 A | 12/1965 | Tate et al. |
| 4,082,881 A | 4/1978 | Chen et al. |
| 4,371,703 A | 2/1983 | Stoss |
| 4,383,051 A | 5/1983 | Meyborg et al. |
| 4,408,061 A | 10/1983 | Salzburg et al. |
| 4,418,174 A | 11/1983 | Dhein et al. |
| 4,529,666 A | 7/1985 | Salzburg et al. |
| 4,564,692 A * | 1/1986 | Feldmann et al. .......... 549/464 |
| 5,766,679 A | 6/1998 | Siemensmeyer et al. |
| 6,013,812 A | 1/2000 | Haas et al. |
| 6,025,061 A | 2/2000 | Khanarian et al. |

FOREIGN PATENT DOCUMENTS

| | | |
|---|---|---|
| EP | 315 334 | 12/1992 |
| GB | 613444 | 11/1948 |
| WO | 99/54129 | 10/1999 |
| WO | 00/14081 | 3/2000 |

OTHER PUBLICATIONS

Patent Abstracts of Japan, vol. 1998; No. 08; Jun. 30, 1998; & JP10059976 (Dainippon Ink et al.).
Patent Abstracts of Japan, vol. 004; No. 124; Sep. 2, 1980; & JP55079383 (Towa Kasei Kogyo KK).
A Derwent Abstract of WO 99/45054.
A Derwent Abstract of EP 380402.
A Derwent Abstract of EP 323994.
A Derwent Abstract of EP 52295.

* cited by examiner

*Primary Examiner*—Shaojia Jiang
*Assistant Examiner*—Ganapathy Krishnan
(74) *Attorney, Agent, or Firm*—Young & Thompson

(57) ABSTRACT

The invention concerns a method for purifying a composition containing at least a product for internal dehydration of a hydrogenated sugar. The invention is characterised in that it comprises: (a) an optional step whereby said composition is treated, whether after re-dissolving or not, with at least a discoloration means; (b) a subsequent step whereby the composition, optionally treated with discoloration means, is treated with at least ion-exchanging means; (c) a subsequent step whereby the resulting composition is treated with at least discoloration means. Said method is in particular applicable to isohexide compositions, in particular isosorbide or isomannide. The resulting compositions, which exhibit particular characteristics in terms of purity and proportion of some impurities, constitute novel products for use in chemical, pharmaceutical, cosmetology and food industries.

15 Claims, No Drawings

METHOD FOR PURIFYING A COMPOSITION CONTAINING AT LEAST ONE INTERNAL DEHYDRATION PRODUCT OF A HYDROGENATED SUGAR

CROSS REFERENCE TO RELATED APPLICATIONS

This application is a Continuation application of PCT/FR01/01676 filed May 30, 2001, which claims priority of French Patent Application No. 00 07463 filed Jun. 9, 2000, which are included in their entirety by reference made hereto.

The present invention relates to a novel method for purifying a composition containing at least one internal dehydration product of a hydrogenated sugar.

It also relates to the use of the purified composition thus obtained in the preparation of polymeric or nonpolymeric, biodegradable or nonbiodegradable products or mixtures intended in particular for the chemical, pharmaceutical, cosmetic or food industries.

Finally, the present invention also relates to a novel product which can be obtained according to said method, a composition of the type in question having specific characteristics in terms of purity and content of certain impurities.

The expression "hydrogenated sugar" for the purposes of the present invention is understood to mean in particular:
hexitols such as, for example, sorbitol, mannitol, iditol and galactitol,
pentitols such as, for example, arabitol, ribitol and xylitol, and
tetritols such as, for example, erythritol.

The expression "internal dehydration product" is understood to mean any product resulting, in any manner, in one or more steps, from the removal of one or more molecules of water from the original internal structure of a hydrogenated sugar such as those mentioned above.

This may be advantageously internal dehydration products of hexitols, in particular of dianhydrohexitols or "isohexides" such as isosorbide (1,4-3,6-dianhydrosorbitol), isomannide (1,4-3,6-dianhydromannitol) or isoidide (1,4-3,6-dianhydroiditol).

Among these doubly dehydrated hydrogenated sugars, isosorbide is currently the one for which the largest number of industrial applications is being developed, or at the very least envisaged. They relate to in particular:
the preparation of isosorbide 2-nitrate, 5-nitrate or 2,5-dinitrate, which are useful in the therapeutic treatment of diseases, in particular cardiac and/or vascular diseases—as described in U.S. Pat. No. 4,371,703;
the preparation of alkylated, in particular dimethylated, derivatives of isosorbide, which are useful in particular as solvents in the context of the preparation of pharmaceutical or cosmetic compositions (U.S. Pat. No. 4,082,881), or even as active ingredients in compositions for oral hygiene (EP patent 315 334);
the preparation of articles based on polyvinyl alcohol (U.S. Pat. No. 4,529,666), polyurethanes (U.S. Pat. No. 4,383,051), or polyesters also containing monomer units of the "terephthaloyl" type (patents U.S. Pat. No. 3,223,752 and U.S. Pat. No. 6,025,061);
the preparation of biodegradable polycondensates (patent WO 99/45 054);
the preparation of aqueous lacquers (U.S. Pat. No. 4,418,174) or of compositions with surface covering and/or coloring action (U.S. Pat. No. 5,766,679).

For the majority of the abovementioned applications of isosorbide and other internal dehydration products of hydrogenated sugars, in particular of the other isohexides, it is generally required to apply a purification treatment to the compositions resulting directly from the actual dehydration step. That is in particular because any hydrogenated sugar subjected to such a step (for example sorbitol) is likely, during said step, to be converted to, apart from the desired dehydration product (for example isosorbide), various coproducts such as:
isomers of said desired product, for example isomers of isosorbide such as isomannide and isoidide,
products which are less dehydrated than the desired product or than its isomers, for example sorbitan, mannitan or iditan,
  derivatives resulting from the oxidation or more generally from the degradation of the abovementioned products, it being possible for these derivatives to include, for example when the desired product is isosorbide, coproducts of the type such as deoxymonoanhydrohexitols, monoanhydropentitols, monoanhydrotetritols, anhydrohexoses, hydroxymethylfurfural, or glycerin,
derivatives resulting from the polymerization of the abovementioned products, and/or
highly colored species of a poorly defined nature.

It should be recalled that in general, all or some of these various categories of coproducts or impurities are generated to a greater or lesser degree during the actual step of dehydration of the hydrogenated sugar, this being independently of the conditions and precautions used in practice during said step, and for example independently:
of the nature and of the form of presentation of the dehydration acid catalyst used (inorganic acid, organic acid, cationic resin, and the like), or
of the quantity of water or of organic solvent(s) in the initial reaction medium, or
of the purity of the hydrogenated sugar composition, for example of sorbitol, used as raw material.

Various technologies have been recommended for the purposes of obtaining compositions derived from said dehydration step, for example compositions of isohexide(s), which are improved in terms of purity, this being in a "direct" manner by adjusting the reaction conditions during said step and/or in an "indirect" manner by applying one or more purification treatments after said step.

By way of example, GB patent 613,444 describes the production, by dehydration in a water/xylene medium, of an isosorbide composition which is then subjected to a treatment of distillation and then of recrystallization from an alcohol/ether mixture.

A purification treatment combining distillation and recrystallization from a lower aliphatic alcohol (ethanol, methanol) has also been recently recommended in patent WO 00/14081. This document moreover indicates that in the case where distillation is the only purification step envisaged, it is advantageous to carry out said step in the presence of sodium borohydride.

Other authors have also recommended that the distillation step be carried out in the presence of a boron-containing compound, in particular of boric acid or of an anionic resin previously charged with borate ions, as described in U.S. Pat. No. 3,160,641.

Patents U.S. Pat. No. 4,408,061 and EP 323,994 envisage the use of particular dehydration catalysts (gaseous hydrogen halide and liquid hydrogen fluoride respectively), advantageously combined with carboxylic acids as cocatalysts followed by the distillation of the crude isosorbide or isomannide compositions thus obtained.

U.S. Pat. No. 4,564,692 mentions, without giving any details, prepurification on "ion exchangers and/or activated charcoal" of isosorbide or isomannide compositions followed, after concentration by evaporation and seeding of crystals of the desired isohexide, by crystallization thereof from water.

EP patent 380,402 claims, for its part, the dehydration of hydrogenated sugars in the presence of hydrogen under pressure and of particular catalysts based on a combination between copper and a noble metal of Group VIII or gold. These conditions are presented as making it possible to significantly reduce the formation of impurities of a polymeric nature during the actual dehydration step.

More recently, there has been described in EP patent 915,091 the possibility of further advantageously reducing the genesis of such undesirable polymers, this being by using acid-stable hydrogenation catalysts during the dehydration step.

The result of the preceding step is that the production of compositions of high purity based on isohexide(s) or other dehydrated hydrogenated sugar(s) generally requires the use, at least at a given moment, of means which are, at the very least:

either expensive such as the hydrogen associated with hydrogenation catalysts and cocatalysts, or potentially dangerous for humans and the environment, in any case whose use is highly regulated, such as organic solvents, or not very effective in terms of yield such as the technology of crystallization from water.

In addition, the abovementioned patents do not generally deal with the problem of stability over time of the purified compositions obtained, including those which were more or less decolorized during the purification treatment.

According to the applicant, it has in fact so far not been possible in industrial practice to effectively prepare compositions, for example of isosorbide, having simultaneously a purity of at least 98.5% (dry/dry), a white color (as a powder) or colorless (as a solution) and good stability, without requiring successively a step of distillation followed by a step of crystallization from an organic solvent medium.

Indeed, the alternative route consisting of a simple distillation of the medium derived from the step of dehydration and its conversion, by cooling, to a "massecuite" type composition does not make it possible to obtain satisfactory results in terms of purification, in particular of coloration (yellow to brown color) and of stability. The use, before evaporation, of an additional step of treatment with granular activated charcoal of a distillate redissolved beforehand, makes it possible to obtain an improved composition in terms of color but not at all in terms of purity. Furthermore, such a composition has a relatively limited stability over time. The applicant company has found, after numerous research studies, that it was possible to obtain compositions based on isohexide(s) and other dehydrated hydrogenated sugars, of high purity (including greater than or equal to 99.5%) and improved stability, without necessarily involving a step of crystallization from a solvent medium, this being using, in a particular order, at least one decolorization treatment step and at least one ion-exchange step.

More precisely, the subject of the present invention is a method for purifying a composition containing at least one internal dehydration product of a hydrogenated sugar, characterized in that it comprises:

a) an optional step during which said composition is treated, after redissolving or not, with at least one decolorizing means, b) a subsequent step during which the composition, optionally treated with a decolorizing means, is treated with at least one ion-exchange means, and c) a subsequent step during which the resulting composition is treated with at least one decolorizing means.

According to one advantageous variant of said method, the latter is characterized in that it comprises:

a) a step during which the composition, which has been redissolved or not, is treated with activated charcoal, b) a subsequent step during which the resulting composition is treated with at least one ion-exchange means, c) a subsequent step during which the resulting composition is treated with activated charcoal.

Still more preferably, the activated charcoal used:
during step a) is in granular form,
during step c) is in pulverulent form.

According to another variant, the ion-exchange means used during step b) comprises at least one anionic resin and at least one cationic resin. Preferably, this means is composed of a mixed bed of anionic resin(s) and, cationic resin(s) or a succession of cationic resin(s) followed by anionic resin(s) or a succession of cationic resin(s) followed by anionic resin(s). In a very advantageous manner, the resins used are strong cationic resin(s) and strong anionic resin(s).

According to another embodiment of the method according to the invention, it comprises a step d) during which the composition resulting from step c) is subjected, after optional filtration, to a concentration treatment in order to obtain a "massecuite" product optionally followed by crystallization treatment, in particular from an organic solvent medium and/or drying.

The compositions subjected to the method of purification according to the invention contain at least one internal dehydration product of a hydrogenated sugar as defined above, it being possible for the dehydration to be total or partial.

In general, said compositions contain a mixture of several of these products in which one of them is predominant on a weight basis. The first aim of the method of purification according to the invention is to confer on these compositions improved properties in terms of stability and coloration, while preserving, and optionally increasing, the proportion by weight of the particular hydrogenated sugar in relation to all the other species contained in the dry matter ("DM") content of said compositions.

These compositions may be obtained according to any one of the dehydration, optionally followed by distillation, steps described in any one of the abovementioned patents. The method according to the invention is nevertheless also advantageously applicable, if desired, to compositions already purified by crystallization from a solvent medium or from water and which, in this case, are generally redissolved so as to be treated in accordance with the invention.

The composition subjected to the method of purification according to the invention may advantageously consist of an isohexide composition, namely a composition, regardless of its origin, its nature, its form of presentation, and its composition, containing an isohexide in the form of a mixture or not with one or more other isohexides, said isohexide being in any case the species which is the most present and which is generally dominant in the DM contained in said composition.

According to the nature of the isohexide which is thus predominant on a weight basis, this may include in particular an isosorbide, isomannide, isoidide or isogalactide composition.

According to a preferred variant, the composition subjected to the method of purification according to the invention consists of an isosorbide composition.

The applicant company has found that, remarkably, the method of purification as claimed, namely combining the successive use of an ion-exchange means followed by decolorization, made it possible to obtain improved compositions in terms of stability.

The expression "stability" is understood to mean in particular the stability over time of the composition in terms of variation of the pH, the conductivity and/or the content of certain impurities. These include in particular formic acid and, in general, ionic species, all these products not having been specifically studied in the abovementioned prior art. The applicant company thinks that in any case, all or some of these products could play the role of "promoters" and/or of "indicators" of the instability of the compositions envisaged here.

This result is all the more surprising since the work carried out by the applicant has shown that the decolorization and ion-exchange means used not only individually but also combined in a reverse order (decolorization followed by ion exchange), did not at all make it possible to obtain the same performances, in particular in terms of stability of the resulting purified composition.

It was, for example, observed that the treatment of an isosorbide composition passed beforehand through a granular activated charcoal column, through a succession of strong cationic resins followed by strong anionic resins had, in the end, a destabilizing effect on the decolorized isosorbide composition thus obtained. The applicant has found in particular that such a use, not in accordance with the invention, had the unfavorable effect of increasing the propensity of the isosorbide composition 1) to become globally acidified (measurement of the pH) and in particular 2) to generate formic acid but also 3) to generate ionic species (overall measurements of the conductivity), during a storage of even a short duration (2 days) at a relatively low temperature (60° C.).

The fact that a second decolorizing means, in this case pulverulent activated charcoal, is used before the treatment on resins did not make it possible to significantly reduce this propensity.

By contrast, the fact that the same activated charcoal is used after the same treatment on resins, this being in accordance with the present invention, strangely made it possible to obtain an isosorbide composition which, during the same storage treatment, showed a much less marked propensity to become acidified and to generate formic acid and ionic species.

Accordingly, a simple and effective means is henceforth available for preparing improved compositions of isohexides and other dehydrated hydrogenated sugars (sorbitan, mannitan, iditan, galactitan, xylitan, ribitan or erythritan), in particular improved compositions of isosorbide and isomannide.

This means allows in particular the production of isosorbide or isomannide compositions having:

an isosorbide or isomannide purity at least equal to 98.5%, preferably at least equal to 99.0%, expressed as dry weight relative to the total dry weight of said composition, and a content of formic acid, in free and/or salt form, at most equal to 0.01%, also expressed as dry weight relative to the total dry weight of said composition, preferably, a conductivity at most equal to 20 microsiemens per centimeter (20 µS/cm).

Said conductivity is measured according to a test A consisting in adjusting, if necessary, the dry matter (DM) content of the isosorbide composition to a value of 5% by diluting said composition in distilled water or, conversely, by concentrating it under vacuum and then by measuring the conductivity of the 5% composition thus obtained.

Remarkably, this means allows, in particular in combination with a preceding or subsequent crystallization step, the production of isosorbide compositions thus characterized and having a purity at least equal to 99.5%, preferably at least equal to 99.6% and for example of the order of 99.8% as will be moreover exemplified.

The method according to the invention also allows the production of isosorbide or isomannide compositions having an isosorbide or isomannide purity at least equal to 98.5%, preferably at least equal to 99.0%, a total monoanhydropentitol content at most equal to 0.1%, preferably at most equal to 0.07%, and a total monodeoxy- and dideoxymonoanhydrohexitol content at most equal to 0.1%, preferably at most equal to 0.08%, these percentages being expressed as dry weight relative to the total dry weight of said composition.

As indicated, this method allows the production of isosorbide compositions thus characterized and having a purity at least equal to 99.5%, preferably at least equal to 99.6%.

The content of isosorbide and other dehydrated hydrogenated sugars is conventionally measured by gas chromatography (GC).

The formic acid content is conventionally measured by high-performance liquid chromatography (HPLC).

To the knowledge of the applicant, isosorbide or isomannide compositions thus characterized constitute novel industrial products. Since they are capable of being obtained in accordance with the invention without necessarily involving the step d) of crystallization from an organic solvent medium, and/or with the use of a final drying step, these compositions may be advantageously free of traces of any organic solvent for certain uses.

The compositions of isosorbide and other internal dehydration products of hydrogenated sugars such as isomannide as obtained according to the invention may be provided in various liquid or solid forms, and in particular in the form of purified distillates, of massecuite products or of compositions of well-individualized crystals. The solid forms may in addition have a white color and a water content at most equal to 1%, preferably at most equal to 0.6% and in particular of between 0.10% and 0.55%.

Taking into account their characteristics of purity, stability and/or color, these compositions may be advantageously used in numerous industries and in particular as synthesis intermediates, comonomer (including chain extending agent), solvent agent, plasticizing agent, lubricating agent, filling agent, sweetener and/or active ingredient, in the preparation of polymeric or nonpolymeric, biodegradable or nonbiodegradable, products or mixtures intended for the chemical, pharmaceutical, cosmetic or food industries.

The present invention will be described in greater detail with the aid of the following examples which are not at all limiting.

EXAMPLE 1

1 kg of a sorbitol solution containing 70% DM, marketed by the applicant under the name "NEOSORB® 70/02" and 7 g of concentrated sulfuric acid are introduced into a jacketed stirred reactor. The mixture obtained is heated under vacuum (pressure of about 100 mbar) for 5 hours so as to remove the water content in the initial reaction medium and that obtained from the sorbitol dehydration reaction.

The crude reaction product is then cooled to around 100° C. and then neutralized with 11.4 g of a 50% sodium hydroxide solution. The isosorbide composition thus neutralized is then distilled under vacuum (pressure of less than 50 mbar).

The slightly colored (light yellow color) crude isosorbide distillate is then dissolved in distilled water so as to obtain a solution containing 40% DM.

This solution is then percolated on a "CECA DC 50" type granular activated charcoal column at a rate of 0.5 BV/h (Bed Volume/hour). The decolorized isosorbide composition thus obtained is then passed, at a rate of 2 BV/h, successively over a column of "PUROLITE C 150 S" type strong cationic resin and then a column of "AMBERLITE IRA 910" type strong anionic resin.

This solution is then treated with "NORIT SX+" type powdered activated charcoal at 20° C. for 1 hour. The activated charcoal is used in an amount of 5% expressed as dry weight/dry weight of solution.

After filtration, the isosorbide solution is concentrated under vacuum. The molten mass obtained crystallizes on cooling in the form of a "massecuite product" of large crystals which are then ground in order to obtain a white powder having a moisture content of 0.3% and therefore a DM of 99.7%.

This isosorbide composition, which is obtained in accordance with the invention, has the characteristics below, the percentages being expressed relative to the total weight of said composition.

| | |
|---|---|
| water | 0.3% |
| isosorbide | 98.8% |
| isomannide | 0.3% |
| other dianhydrohexitols | 0.3% |
| monoanhydropentitols | <0.025% |
| deoxyhexitols | <0.070% |
| formic acid | <0.0005% |
| pH* | 6.6 |
| conductivity* | <20 µS/cm |

*measured after diluting the composition to a DM of 5%.

The composition obtained, in accordance with the invention, therefore has an isosorbide purity of 98.8/99.7, that is about 99.1%.

20 g of this massecuite product of isosorbide are introduced into a stoppered plastic container, itself stored in an oven at 60° C. After 2 days of storage under these conditions, it is noted that this composition has slightly changed in terms of pH (decrease of 0.6 pH unit) but that in particular its isosorbide purity, its formic acid concentration and its conductivity have not significantly changed, the latter two characteristics remaining at a very low level (<0.005% and <50 µS/cm respectively).

EXAMPLE 2

In these tests, the crude isosorbide distillate as obtained in EXAMPLE 1 is purified according to different variants not in accordance with the invention, namely respectively:

TEST 1: the distillate is only treated over granular activated charcoal before being crystallized in the form of a massecuite product, TEST 2: the distillate is only treated over resins (strong cationic followed by strong anionic) before being crystallized (massecuite), TEST 3: the distillate is first treated over activated charcoal and then over resins (strong cationic followed by strong anionic) before being crystallized (massecuite), TEST 4: the distillate is successively treated over granular activated charcoal and then with pulverulent activated charcoal before being filtered and then treated over resins and crystallized (massecuite).

It is observed that all the isosorbide compositions as resulting directly from these methods, have overall:

a pH which is very slightly or which is significantly less than that of the massecuite product obtained in EXAMPLE 1, namely a pH between 5.6 (TEST 2) and about 6.5 (TESTS 3 and 4), a conductivity of less than 20 µS/cm (TESTS 2 to 4), or even slightly higher (23 µS/cm—TEST 1), and a proportion of formic acid of less than 0./0005% or 5 ppm (TESTS 2 to 4), or even slightly higher (0.0015% or 15 ppm—TEST 1).

However, it is observed that, under storage conditions identical to those described for EXAMPLE 1, all these compositions show:

a reduction in pH at least three times that observed in the case of EXAMPLE 1, and in particular 4 times (TEST 4) to 5 times (TEST 3) higher than it, a genesis of formic acid which is much more significant than in the case of EXAMPLE 1, the level of formic acid still exceeding the value of 0.01% and reaching values greater than 0.02% (TEST 4), or even greater than 0.04% (TEST 3) and even to 0.08% (TEST 2).

In addition, the compositions derived from TESTS 2 and 3 show a very marked propensity to generate ionic species during storage since, after only 2 days, their conductivity reaches the value of 40 µS/cm (TEST 3), or even exceeds the value of 80 µS/cm (TEST 2).

Consequently, very surprisingly, the method in accordance with the invention as imagined by the applicant in EXAMPLE 1 and envisaging the use of a decolorization means after an ion exchange means, makes it possible to obtain compositions, in this case of isosorbide, which are much more stable than those obtained according to all the methods described in the present EXAMPLE 2.

This improvement by the use of these two specific means in a particular order is all the more unexpected if the effects obtained respectively either with each of these means taken in isolation (TESTS 1 and 2) or with these means combined but in a reverse order (TESTS 3 and 4) are considered.

EXAMPLE 3

In these tests, in accordance with the invention, a crude distillate of isosorbide is obtained and then treated in the same manner as in EXAMPLE 1, with the exception of certain variants, namely respectively:

TEST 5: the massecuite product as obtained in EXAMPLE 1 is redissolved, in the hot state, in methanol. The resulting solution containing 75% DM is cooled to a temperature of about −15° C. and converts to a composition of crystals which are better individualized than those of the initial massecuite product, TEST 6: the sorbitol composition used as raw material for the actual dehydration step was purified beforehand by chromatography by means of a "PCR 432" type PUROLITE column in calcium form, TEST 7: the distillation step is carried out in 0.5% Na B H$_4$ (dry/dry), TEST 8: the solution containing 40% DM subjected to the treatment on granular activated charcoal and then, in accordance with the invention, on cationic and anionic resins and then on pulverulent activated charcoal, results from the redissolution in water of isosorbide crystals, the latter having been conventionally obtained by crystallization, from methanol, of an isosorbide massecuite product itself obtained by distillation.

All the compositions obtained, in accordance with the invention, have a water content of between 0.1% (TEST 8) and 0.5% (TEST 5) and a purity which is still (slightly) higher than that of the product derived from EXAMPLE 1. This isosorbide purity is between 99.2% (TEST 7) and 99.6% (TESTS 5, 6 and 8).

It is in fact remarkable that such a level of purity (99.6%) can be obtained, in particular, in the absence of any crystallization step in accordance with TEST 6.

This product and those resulting from TESTS 5, 7 and 8 in fact have a good stability during storage and levels of particular impurities in accordance with the present invention.

EXAMPLE 4

The crude distillate, as obtained in EXAMPLE 1, is dissolved in 2-propanol, at a temperature of 60° C., so as to obtain a solution containing 75% dry matter (DM). This solution is then slowly cooled, in a space of 5 hours, at a temperature of 10° C. A recrystallized isosorbide seed is added at 40° C.

The crystals are then drained in a centrifugal apparatus and washed with a small quantity of 2-propanol.

After drying under vacuum, the crystals are redissolved in water so as to obtain a DM of 40%.

This solution is percolated on a column of granular activated charcoal (CPG 12–40) at a rate of 0.5 BV/h. The isosorbide composition thus obtained is then passed, at a rate of 2 BV/h, successively over a column of strong cationic resin followed by a column of strong anionic resin such as those described in EXAMPLE 1 of this patent.

The solution is then treated with NORIT SX+ type powdered activated charcoal at 20° C. for 1 hour. The activated charcoal is used in an amount of 0.2% expressed as dry weight/dry weight of solution.

After filtration, the isosorbide solution is concentrated under vacuum. The molten mass obtained crystallizes on cooling in the form of a massecuite product which is then ground in order to obtain a white powder having a moisture content of 0.2%.

This isosorbide composition, which is obtained in accordance with the invention, has the characteristics below, the percentages being expressed relative to the total weight of said composition.

| | |
|---|---|
| water | 0.2% |
| isosorbide | 99.6% |
| isomannide | not detected |
| other dianhydrohexitols | 0.03% |
| monoanhydropentitols | not detected |
| deoxyhexitols | not detected |
| formic acid | <0.0005% |
| pH* | 6.5 |
| conductivity* | <20 µS/cm |

Its isosorbide purity is therefore 99.6/99.8, that is about 99.8%.

20 g of this isosorbide massecuite product are introduced into a stoppered plastic container which is itself stored in an oven at 60° C. After 14 days of storage, it is noted that its isosorbide purity and its formic acid concentration have not changed.

EXAMPLE 5

700 g of mannitol, 300 g of water and 21 g of concentrated sulfuric acid are introduced into a jacketed stirred reactor. The mixture obtained is heated under vacuum (40 mbar) for 8 hours so as to remove the water contained in the reaction medium and that derived from the mannitol dehydration reaction.

The crude reaction product is neutralized with a 50% sodium hydroxide solution. The isomannide composition is then distilled under vacuum.

The crude distillate is dissolved in water so as to obtain a dry matter content of 40%.

This solution is percolated on a column of granular activated charcoal (CPG 12–40) at a rate of 0.5 BV/h. The isomannide composition thus obtained is then passed, at a rate of 2 BV/h, successively over a column of strong cationic resin followed by a column of strong anionic resin such as those described in EXAMPLE 1.

The solution is then treated with NORIT SX+ type powdered activated charcoal at 20° C. for 1 hour. The activated charcoal is used in an amount of 5% expressed as dry weight/dry weight of solution.

After filtration, the isomannide solution is concentrated under vacuum. The molten mass obtained crystallizes on cooling in the form of a massecuite product which is then ground in order to obtain a white powder having a moisture content of 0.3%.

This isomannide composition, which is obtained in accordance with the invention, has the characteristics below, the percentages being expressed relative to the total weight of said composition.

| | |
|---|---|
| water | 0.5% |
| isomannide | 98.0% |
| isosorbide | 0.9% |
| other dianhydrohexitols | 0.3% |
| formic acid | <0.0005% |
| pH* | 6.5 |
| conductivity* | <20 µS/cm |

Its isomannide purity is therefore 98/99.5, that is about 98.5%.

20 g of this isomannide massecuite product are introduced into a stoppered plastic container which is itself stored in an oven at 60° C. After 14 days of storage, it is noted that its isosorbide purity and its formic acid concentration have not changed.

We claim:

1. A method for purifying a composition containing at least one internal dehydration product of a hydrogenated sugar, said purification process comprising:
   a) distilling said composition,
   b) treating said distilled composition of a), with at least one of a cationic resin and an anionic resin, and
   c) decolorizing the resulting composition obtained from b).

2. The method as claimed in claim 1, wherein the decolorizing is achieved with an activated charcoal.

3. The method as claimed in claim 1, wherein step b) comprises treating with a mixed bed of at least an anionic resin, and at least a cationic resin.

4. The method as claimed in claim 1, further comprising a step d) concentrating the composition resulting from step c), after optional filtration, in order to obtain a massecuite product.

5. The method as claimed in claim 1, wherein the composition containing at least one internal dehydration product of a hydrogenated sugar consists of an isohexide composition.

6. The method as claimed in claim 1, wherein step b) of comprises treating first with at least one cationic resin and then with at least one anionic resin.

7. The method as claimed in claim 1, wherein said cationic resin is a strong cationic resin and said anionic resin is a strong anionic resin.

8. The method as claimed in claim 1, further comprising an additional step prior to step b) of deodorizing said distilled composition of a) with activated charcoal in granular form.

9. The method as claimed in claim 2, wherein the activated charcoal in the step c) is in pulverulent form.

10. The method as claimed in claim 4, wherein the step d) is followed by drying.

11. The method as claimed in claim 1, wherein the composition containing at least one internal dehydration product of a hydrogenated sugar is an isohexide composition selected from the group consisting of isosorbide, isomannide, isoidide and isogalactide compositions.

12. The method as claimed in claim 11, wherein the isohexide composition is selected from the group consisting of isosorbide and isomannide compositions.

13. The method as claimed in claim 1, wherein said at least one internal dehydration product of a hydrogenated sugar is a crude neutralized product.

14. The method as claimed in claim 1, wherein the distilling is carried out under vacuum.

15. The method as claimed in claim 14, wherein the distilling is carried out under pressure of less than 50 mbar.

* * * * *